US006245356B1

(12) United States Patent
Baichwal

(10) Patent No.: US 6,245,356 B1
(45) Date of Patent: *Jun. 12, 2001

(54) SUSTAINED RELEASE HETERODISPERSE HYDROGEL SYSTEMS-AMORPHOUS DRUGS

(75) Inventor: Anand Baichwal, Wappingers Falls, NY (US)

(73) Assignee: Edward Mendell Co., Inc., Patterson, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/498,448

(22) Filed: Feb. 4, 2000

Related U.S. Application Data

(63) Continuation of application No. 09/106,438, filed on Jun. 29, 1998, now Pat. No. 6,048,548, which is a continuation of application No. 08/634,295, filed on Apr. 18, 1996, now Pat. No. 5,773,025, which is a continuation-in-part of application No. 08/447,236, filed on May 22, 1995, now Pat. No. 5,554,387, which is a division of application No. 08/118,924, filed on Sep. 9, 1993, now Pat. No. 5,455,046.

(51) Int. Cl.$^7$ .............................. A61K 9/22; A61K 47/30
(52) U.S. Cl. ........................ 424/468; 424/480; 424/481; 424/482
(58) Field of Search ............................................. 424/468

(56) References Cited

U.S. PATENT DOCUMENTS

| 3,485,847 | 12/1969 | Bossert et al. | 260/295.5 |
|---|---|---|---|
| 3,784,684 | 1/1974 | Bossert et al. | 424/37 |
| 4,191,772 | 3/1980 | Woog et al. | 424/273 R |

(List continued on next page.)

FOREIGN PATENT DOCUMENTS

| 1288049 | 8/1991 | (CA) . | |
|---|---|---|---|
| 2101680 | 2/1994 | (CA) | A61K/31/44 |
| 2714065 | 10/1978 | (DE) | A61K/9/10 |
| 0147171 | 7/1985 | (EP) | C07D/401/12 |
| 3400106 | 7/1985 | (DE) | A61K/9/00 |
| 0234670 | 2/1987 | (EP) . | |
| 0357793 | 3/1990 | (EP) . | |
| 0047899 | 2/1996 | (EP) | A61K/9/14 |
| 0232155 | 8/1997 | (EP) . | |
| 2160100 | 12/1995 | (GB) | A61K/9/22 |
| WO8504100 | 9/1985 | (WO) | A61K/9/40 |
| WO8902738 | 4/1989 | (WO) . | |
| WO9206680 | 4/1992 | (WO) . | |
| WO 9313773 | 7/1993 | (WO) | A61K/31/44 |
| WO9412700 | 10/1994 | (WO) | A61K/9/16 |

OTHER PUBLICATIONS

Chemical Abstracts, vol. 104 (1986) Abstract 174662y.
Chemical Abstracts, vol. 99 (1983) Abstract 128360d.
Chemical Abstracts, vol. 92 (1980) Abstract 135278s.
Chemical Abstracts, vol. 92 (1980) Abstract 82429h.
Chemical Abstracts, vol. 77 (1972) Abstract 39130g.
Chemical Abstracts, vol. 70 (1969) Abstract 17133p.
Chemical Abstracts, vol. 98 (1983) Abstract 221832y.
Alderman, D.A., "A Review of Cellulose Ethers in Hydrophilic Matrices for Oral Controlled–Release Dosage Forms," *Int. J. Pharm. Tech. & Prod. Mfg.*, vol. 5, pp. 1–9 (1984).
Haynes, R. Brian, M.D., et al., "Manipulation of the therapeutic regimen to improve compliance: Conceptions and misconceptions," *Clinical Pharmacology and Therapeutics*, vol. 22, No. 2, (Aug. 1977).
English translation of Japanese Patent Laid–Open–To–Public, publication No. 8/1986, publication date Jan. 6, 1986, Japanese Patent Application No. 118,789/1984; Japanese Patent Application date: Jun. 9, 1984.
*Techniques of Solubilization of Drugs*, edited by Samuel H. Yalkowsky, The Upjohn Company, pub. Marcel Dekker, Inc., New York and Basel, pp. 308–315 (1981).
"Crystallization and Granulation," Remington's Practice of Pharmacy, 9$^{th}$ Ed. Chapter XXVII, pp. 208–211, 1950.
Ritschel, Angewandte Blopharmazie, pp. 293–302 (1973).
Sugimoto, I., et al., "Dissolution and Absorption of Nifedipine from Nifedipine–Polyvinylpyrrolidone Coprecipitate", *Drug Development and Industrial Pharmacy*, vol. 6, No. 2, pp. 137–161 (1980).
Kleinblosem, M., et al., Nifedipine: Kinetics and dynamics in healthy subjects, *Clin. Pharmacol. Ther.*, Vo. 35, No. 6, pp. 742–749 (1984).
Ramasch, K., et al., "Pharmacokinetics and Metabolism of Nifediphine", *Hypertension Supplement II*, Vo. 5, No. 4, Jul.–Aug. 18–24 (1983).
McGinity, J.W., et al., "Dissolution and Uniformity Properties of Ordered Mixes of Micronized Griseofulvin and a Directly Compressible Excipient", *Drug Development and Industrial Pharmacy*, vol. 11, No. 4, pp. 891–900 (1985).
Helbig, J., et al. "Pharmaceutical oral dosage forms of an active agent capable of forming or releasing bicarbonate ions", *Pharmaceuticals*, (Abstract–98:221837d), vol. 98, p. 63 (1983).
The Merck Index, pp. 848–849, 9$^{th}$ Ed. (1976).
D.Q.M. Craig, "Polyethyelene Glycols and Drug Release", *Drug Development and Industrial Pharmacy*, 16(17), pp. 2501–2526 (1990).
Derwent Abstract DE 3400106A.

*Primary Examiner*—Peter F. Kulkosky
(74) *Attorney, Agent, or Firm*—Davidson, Davidson & Kappel, LLC

(57) ABSTRACT

Sustained release oral solid dosage forms comprising agglomerated particles of a therapeutically active medicament in amorphous form, a gelling agent, an ionizable gel strength enhancing agent and an inert diluent, as well as processes for preparing and using the same are disclosed. The sustained release oral solid dosage forms are useful in the treatment of hypertension in human patients.

30 Claims, No Drawings

U.S. PATENT DOCUMENTS

| | | | |
|---|---|---|---|
| 4,346,709 | 8/1982 | Schmitt | 128/260 |
| 4,412,986 | 11/1983 | Kawata et al. | 424/80 |
| 4,562,069 | 12/1985 | Hegasy et al. | 424/80 |
| 4,665,081 | 5/1987 | Doi et al. | 514/356 |
| 4,673,564 | 6/1987 | Kawata et al. | 424/494 |
| 4,696,815 | 9/1987 | Schepky et al. | 424/80 |
| 4,764,382 | 8/1988 | Kydonieus et al. | 424/449 |
| 4,765,989 | 8/1988 | Wong et al. | 424/473 |
| 4,765,990 | 8/1988 | Sugimoto et al. | 424/494 |
| 4,792,448 | 12/1988 | Ranade | 424/438 |
| 4,792,450 | 12/1988 | Kydonieus et al. | 424/449 |
| 4,792,452 | 12/1988 | Howard et al. | 424/475 |
| 4,803,076 | 2/1989 | Ranade | 424/438 |
| 4,803,081 | 2/1989 | Falk et al. | 424/488 |
| 4,808,413 | 2/1989 | Joshi et al. | 424/458 |
| 4,851,229 | 7/1989 | Magruder et al. | 424/457 |
| 4,867,985 | 9/1989 | Heafield et al. | 424/461 |
| 4,880,623 | 11/1989 | Pierigiogio et al. | 424/78 |
| 4,889,723 | 12/1989 | Kim et al. | 424/450 |
| 4,892,741 | 1/1990 | Ohm et al. | 424/479 |
| 4,894,235 | 1/1990 | Kohne et al. | 424/452 |
| 4,904,699 | 2/1990 | Bauer | 514/972 |
| 4,940,587 | 7/1990 | Jenkins et al. | 424/480 |
| 4,942,040 | 7/1990 | Ragnarsson et al. | 424/486 |
| 4,973,469 | 11/1990 | Mulligan et al. | 424/461 |
| 4,983,593 | 1/1991 | Miyajima et al. | 514/110 |
| 4,994,276 | 2/1991 | Baichwal et al. | 424/440 |
| 5,007,790 | 4/1991 | Shell | 424/451 |
| 5,015,479 | 5/1991 | Mulligan et al. | 424/457 |
| 5,019,397 | 5/1991 | Wong et al. | 424/473 |
| 5,024,843 | 6/1991 | Kuczynski et al. | 424/499 |
| 5,051,263 | 9/1991 | Barry et al. | 424/490 |
| 5,071,642 | 12/1991 | Lahr et al. | 424/474 |
| 5,071,643 | 12/1991 | Yu et al. | 514/570 |
| 5,091,190 | 2/1992 | Kuczynski et al. | 424/473 |
| 5,093,198 | 3/1992 | Speaker et al. | 428/402 |
| 5,096,714 | 3/1992 | Kuhrts | 424/439 |
| 5,100,669 | 3/1992 | Hyon et al. | 424/426 |
| 5,108,757 | 4/1992 | Erdos et al. | 424/451 |
| 5,110,602 | 5/1992 | Kim et al. | 424/451 |
| 5,128,142 | 7/1992 | Mulligan et al. | 424/457 |
| 5,128,143 | 7/1992 | Baichwal et al. | 424/464 |
| 5,132,116 | 7/1992 | Soumac et al. | 424/469 |
| 5,133,974 | 7/1992 | Paradissis et al. | 424/480 |
| 5,135,757 | 8/1992 | Baichwal et al. | 424/465 |
| 5,145,683 | 9/1992 | Rhodes | 424/451 |
| 5,160,734 | 11/1992 | Ganesan et al. | 424/78.38 |
| 5,169,638 | 12/1992 | Dennis et al. | 424/457 |
| 5,169,639 | 12/1992 | Baichwal | 424/468 |
| 5,211,954 | 5/1993 | Sterling et al. | 424/452 |
| 5,211,957 | 5/1993 | Hagemann et al. | 424/466 |
| 5,215,758 | 6/1993 | Krishnamurthy | 424/488 |
| 5,258,185 | 11/1993 | Bauer et al. | 424/484 |
| 5,264,446 | 11/1993 | Hegasy et al. | 514/356 |
| 5,264,459 | 11/1993 | Chelmick-Schorr, et al. | 514/646 |
| 5,273,760 | 12/1993 | Oshlack et al. | 424/480 |
| 5,286,493 | 2/1994 | Oshlack et al. | 424/468 |
| 5,288,500 | 2/1994 | Ibsen | 424/489 |
| 5,292,534 | 3/1994 | Valentine et al. | 424/451 |
| 5,356,467 | 10/1994 | Oshlack et al. | 106/153 |
| 5,415,871 | 5/1995 | Pankhania et al. | 424/481 |
| 5,439,687 | 8/1995 | Compassi | 424/468 |
| 5,455,046 | 10/1995 | Baichwal | 424/457 |
| 5,472,711 | 12/1995 | Baichwal | 424/468 |
| 5,476,654 | 12/1995 | Conte et al. | 424/78.08 |
| 5,478,574 | 12/1995 | Baichwal et al. | 424/485 |
| 5,512,297 | 4/1996 | Baichwal | 424/451 |
| 5,518,730 | 5/1996 | Fuisz | 424/426 |
| 5,554,387 | 9/1996 | Baichwal | 424/488 |
| 5,662,933 | 9/1997 | Baichwal et al. | 424/457 |
| 5,667,801 | 9/1997 | Baichwal | 424/457 |
| 5,670,168 | 9/1997 | Baichwal et al. | 424/464 |
| 5,773,025 | * 6/1998 | Baichwal | 424/458 |
| 5,830,497 | 11/1998 | Yamamaha et al. | 424/448 |
| 5,846,563 | 12/1998 | Baichwal | 424/457 |
| 6,048,548 | * 4/2000 | Baichwal | 424/468 |

\* cited by examiner

SUSTAINED RELEASE HETERODISPERSE HYDROGEL SYSTEMS-AMORPHOUS DRUGS

This application is a continuation of U.S. Ser. No. 09/106,438, filed Jun. 29, 1998, now U.S. Pat. No. 6,048,548 which is a continuation of U.S. Ser. No. 08/634,295, filed Apr. 18, 1996, now U.S. Pat. No. 5,773,025, which is a continuation-in-part of U.S. Ser. No. 08/447,236, filed May 22, 1995, now U.S. Pat. No. 5,554,387, which is a divisional application of U.S. Ser. No. 08/118,924, filed Sep. 9, 1993, now U.S. Pat. No. 5,455,046, the disclosures of which are incorporated herein by reference in their entireties.

BACKGROUND OF THE INVENTION

The advantages of controlled release products are well known in the pharmaceutical field and include the ability to maintain a desired blood level of a medicament over a comparatively longer period of time while increasing patient compliance by reducing the number of administrations necessary to achieve the same. These advantages have been attained by a wide variety of methods. For example, different hydrogels have been described for use in controlled release medicines, some of which are synthetic, but most of which are semi-synthetic or of natural origin. A few contain both synthetic and non-synthetic material. However, some of the systems require special process and production equipment, and in addition some of these systems are susceptible to variable drug release.

Oral controlled release delivery systems should ideally be adaptable so that release rates and profiles can be matched to physiological and chronotherapeutic requirements. While many controlled and sustained release formulations are already known, certain moderately to poorly soluble drugs present formulation difficulties which render them inapplicable for sustained release formulations which might be suitable for, e.g., relatively soluble drugs. It is often not possible to readily predict whether a particular sustained release formulation will provide the desired sustained release for a relatively insoluble drug, and it has generally been found that it is necessary to carry out considerable experimentation to obtain sustained release formulations of such drugs having the desired bioavailability when ingested, particularly for drugs that are poorly soluble in water.

An example of a poorly soluble drug is nifedipine. Nifedipine often exhibits poor bioavailability when incorporated into sustained release formulations. Accordingly, a great deal of attention has been given to the preparation of sustained release nifedipine formulations which provide acceptable bioavailability. U.S. Pat. No. 4,765,989 (Wong, et al.) describes an osmotic system wherein nifedipine is contained along with osmopolymers in a compartment enclosed by a wall which is substantially impermeable to the passage of tile drug. The osmopolymer exhibits an osmotic pressure gradient across the wall against the external fluid. A passageway in the wall communicates with the first composition and the exterior of the device for delivering nifedipine to the passageway.

Other techniques which have been described for preparing sustained release nifedipine formulations include the transformation of crystalline nifedipine into fine powder, the transformation of the crystalline nifedipine to the amorphous form, the formation of clathrates or compounds of inclusion with betacyclodextrines, and the formation of solid solutions with polyethylene glycols ("PEGs").

Still other techniques are directed to processes for increasing the bioavailability of nifedipine. U.S. Pat. No. 4,880,623 (Piergiorgio, et al.) describes a process wherein nifedipine and polyethylene glycol are coprecipitated from a solution into a product in the form of very fine particles having an extremely high total specific surface. In one embodiment, substances which swell upon contact with the gastrointestinal juices and successively dissolve slowly (selected from hydroxypropylmethyl cellulose, methyl cellulose, hydroxypropyl cellulose, carboxyvinyl polymers, xanthan gum) in quantities from 5–50% of the tablet are added so as to obtain the prolongation of the retard effect.

Falk, et al., U.S. Pat. No. 4,803,081, describes compositions and processes for preparing controlled release formulations that include low solubility active ingredients, such as nifedipine, dissolved in a liquid or semi-solid solubilizing agent and further in a controlled release system that does not include locust bean gum.

Mulligan et al., in U.S. Pat. Nos. 4,973,469 and 5,128,142 (assigned to the Elan Corporation) describes compositions and processes for preparing controlled release formulations that include an adsorbate prepared from a mixture of a pharmaceutically useful active ingredient, e.g., nifedipine, and an inactive substance adsorbed on a cross-linked polymer. The formation of the adsorbate is stated to render the active ingredient into an amorphous form. The inactive substance can be, e.g., water insoluble polymers such as polyvinyl alcohol, polyvinylpyrrolidone and hydroxyethylcelluose.

Rhodes in U.S. Pat. No. 5,145,683 (assigned to Ethical Pharmaceuticals, Ltd.) describes amorphous nifedipine prepared as finely divided particles of 100 microns or less as a composition that includes polyvinylpyrrolidone (PVP) in a weight ratio of 10 to 90 percent relative to the weight of nifedipine. Nifedipine coated carrier particles are prepared by mixing nifedipine with polyvinylpyrrolidone and acrylic-based polymer in a solvent, e.g., ethanol. The mixture is then coated onto a water soluble carrier followed by evaporation of the solvent to provide what is asserted to be an amorphous nifedipine coating of water soluble carrier particles.

Hegasy et al. in U.S. Pat. No. 4,562,069 (assigned to Bayer Aktiengesellschaft) discloses formulations including combinations of crystalline and non-crystalline nifedipine. The Hegasy dosage form is described as a "two-phase" formulation including a nifedipine coprecipitate in which the nifedipine is present in both a crystalline and noncrystalline form. The Hegasy formulation is prepared by dissolving nifedipine and the coprecipitate (e.g., PVP, methylcellulose, hydroxypropylcellulose and hydroxypropylmethylcellulose) in a suitable organic solvent (e.g., ethanol) and the remaining solid precipitation is comminuted.

Previously, heterodisperse polysaccharide excipient systems and controlled release oral solid dosage forms were described in U.S. Pat. Nos. 4,994,276, 5,128,143, and 5,135,757. These systems are commercially available under the tradename TIMERx™ from Edward Mendell Co., Inc., Patterson, N.Y., which is the assignee of the present invention. These patents are hereby incorporated by reference.

OBJECTS AND SUMMARY OF THE INVENTION

Accordingly, it is an object of the present invention to provide a sustained release formulation for an insoluble therapeutically active medicament.

It is a further object of the present invention to provide a method for preparing a bioavailable sustained release formulation for an poorly soluble therapeutically active medicament.

It is yet another object of the present invention to provide a sustained release excipient which may be used in the preparation of a sustained release oral solid dosage form of a poorly soluble therapeutically active medicament.

It is a further object of the present invention to provide a sustained release excipient which is suitable for providing, when combined with a medicament in amorphous form, a sustained release formulation which provides therapeutically effective blood levels of the medicament for e.g., ranging from about 12 to about 24 hours.

It is a further object of the present invention to provide a sustained release drug delivery system wherein acceptable bioavailability of an otherwise poorly bioavailable therapeutically active agent is achieved.

The above-mentioned objects and others are achieved by virtue of the present invention, which relates in part to a controlled release formulation comprising a therapeutically effective amount of a medicament in amorphous form having a solubility less than about 10 g/l (e.g., in water), and a controlled release excipient comprising a gelling agent, an inert diluent, and an effective amount of a pharmaceutically acceptable ionizable gel strength enhancing agent suitable for modifying the release rate from the gel which is formed when the controlled release formulation is exposed to an environmental fluid.

More particularly, the present invention is related to a sustained release oral solid dosage form comprising an effective amount of a medicament in amorphous form having a solubility of less than about 10 g/l to render a therapeutic effect; a sustained release excipient comprising a gelling agent, an inert pharmaceutical diluent, and an effective amount of a pharmaceutically acceptable ionizable gel strength enhancer which increases the gel strength of the formulation and thereby desirably controls the release of medicament from the gel to provide a sustained release of the medicament, when the dosage form is exposed to an environmental fluid. The ratio of medicament to gelling agent is preferably from about 1:3 to about 1:8. The sustained release solid dosage form preferably provides a therapeutically effective blood level of the medicament for at least about 12 hours or more, and in certain preferred embodiments, for up to about 24 hours. The active medicament is rendered amorphous by dispersion into a mixture comprising, e.g., a solid solubilizing agent. The present invention is also related to a method for providing a sustained release formulation of a medicament having poor solubility in water, including preparing a sustained release excipient including from about 10 to about 99% by weight of a gelling agent, from about 1 to about 20% by weight of an ionizable gel strength enhancing agent which is increases the gel strength of the gel matrix, and from about 0 to about 89% by weight of an inert pharmaceutical diluent; adding an effective amount of a medicament having a solubility of less than about 10 g/l to render a desired therapeutic effect, and thereafter tableting the resulting mixture such that a product is obtained having a ratio of medicament to gelling agent from about 1:3 to about 1:8. The resulting tablet provides therapeutically effective blood levels of the medicament for at least about 12 hours, and preferably about 24 hours. A gel matrix is created by exposure of the gelling agent to an environmental fluid (e.g., gastrointestinal fluid or an in-vitro dissolution bath).

The present invention is further related to a sustained release oral solid dosage form for absorption of a therapeutically active medicament in the gastrointestinal tract, comprising an agglomerated particle. The agglomerated particle includes a medicament and a sustained release excipient. The sustained release excipient is comprised of a gelling agent that is in turn comprised of xanthan gum and locusts bean gum, providing a controlled release gel when exposed to environmental fluids according to the invention. The sustained release excipient also preferably includes an inert pharmaceutical diluent, the ratio of the inert diluent to said gelling agent being from about 1:8 to about 8:1.

In preferred embodiments, the ratio of the xanthan gum to the locust bean gum is from about 1:3 to about 3:1. In such embodiments, the ionizable gel enhancing agent enhances the strength of the cross-linking between the xanthan gum and locust bean gums.

The present invention also provides a method of producing a sustained release solid oral dosage form by e.g., preparing a formulation including a medicament of low aqueous solubility and the sustained release excipient described above.

In certain preferred embodiments, nifedipine is prepared in amorphous form prior to incorporation into the dosage form. Amorphous nifedipine is prepared by solubilizing or dispersing nifedipine crystals in a vehicle, including, e.g., preferably a solid solubilizing agent, prior to incorporation into the formulation. The present invention is further related to a method of treating a patient by orally administering an oral solid dosage form preferred as set forth above.

In certain preferred embodiments, the mixture of the gelling agent, inert diluent, and ionizable gel strength enhancing agent are optionally granulated with a dispersion or solution of a pharmaceutically acceptable hydrophobic material in an amount sufficient to slow the hydration of the gelling agent without disrupting the gel matrix thus formed.

While the medicament can be any drug with a solubility of less than 10 g/l in aqueous solution, in a particularly preferred embodiment, the medicament comprises a therapeutically effective dihydropyridine, such as e.g., nifedipine that is prepared in amorphous form, e.g., as amorphous particles.

By "sustained release" it is meant for purposes of the present invention that the therapeutically active medicament is released from the formulation at a controlled rate such that therapeutically beneficial blood levels (but below toxic levels) of the medicament are maintained over an extended period of time ranging from e.g., about 12 to about 24 hours, thus, providing, for example, a 12 hour or a 24 hour dosage form.

By "bioavailable" it is meant for purposes of the present invention that the therapeutically active medicament is released from the sustained release formulation and becomes available in the body at the intended site of drug action. By "poorly soluble", it is meant that the therapeutically active medicament has an aqueous solubility of less than about 1000 milligrams per liter (mg/l).

By "moderately soluble", it is meant that the therapeutically active medicament has an aqueous solubility of less than about 10 grams per liter (g/l).

The term "environmental fluid" is meant for purposes of the present invention to encompass, e.g., an aqueous solution, or gastrointestinal fluid or, in vitro, dissolution media used for, e.g., confirmation of the dissolution properties of the formulation.

By "increasing the gel strength", it is meant that the ionizable gel strength enhancing agent interacts with the gelling agent used in the sustained release excipient in such a manner as to desirably prolong the release of drug from the formulation when the formulation is exposed to, e.g., gastrointestinal fluid, and further it is meant that the hydration of the gel and the gel strength provide a desired release rate of drug from the dosage without, for example allowing a phenomena known as dose-dumping.

By the term "dose-dumping" it is meant that the dosage form undesirably releases too much of the drug into the environmental fluid at too early a time after exposure into the environmental fluid. In other words, the dosage-form would thereby not be capable of providing the desired sustained release and sustained effect in-vivo.

DETAILED DISCLOSURE OF THE INVENTION

In the present invention, it has been determined that the gelling agent may be comprised of materials suitable for providing a controlled release gel when exposed to environmental fluids according to the invention. It has been found that a sustained release excipient comprising only a gelling agent (e.g. a hydrophilic gum) may not be sufficient to provide a suitable sustained release of an insoluble medicament to provide a 24 hour formulation, nor to prevent an initial "burst" (i.e., dose dumping) of drug release from the formulation when the formulation is exposed to a fluid in an environment of use, e.g. an aqueous solution or gastrointestinal fluid. This is especially the case with certain medicaments such as those which are only moderately soluble, and is especially true with drugs such as nifedipine which are only poorly soluble.

In a most preferred embodiment the gelling agent comprises a mixture of a xanthan gum and a locust bean gum capable of cross-linking with the xanthan gum when the gums are exposed to an environmental fluid. In this most preferred embodiment the ionizable gel enhancing agent acts to enhance the strength of cross-linking between the xanthan gum and the locust bean gum and thereby prolong the release of the medicament component of the formulation.

Acceptable gelling agents which may also be used, in addition to xanthan gum and locust bean gum, in the present invention include those gelling agents well-known in the art. Examples include naturally occurring or modified naturally occurring gums such as alginates, carrageenan, pectin, guar gum, modified starch, hydroxypropylmethylcellulose, methylcellulose, and other cellulosic materials or polymers, such as sodium carboxymethylcellulose and hydroxypropyl cellulose and mixtures of the foregoing. This list is not meant to be exclusive.

Xanthan gum is a high molecular weight (>$10^6$) heteropolysaccharide. Other preferred heteropolysaccharides include derivatives of xanthan gum, such as deacylated xanthan gum, the carboxymethyl ether, and the polyethylene glycol ester that may be readily substituted for xanthan gum.

The controlled release properties of the formulations of the present invention may be optimized when the ratio of xanthan gum to locust bean gum is about 1:1, although xanthan gum in an amount of from about 20 to about 80 percent or more by weight of the locust bean gum provides an acceptable slow release product.

The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract. Such embodiments of gelling agents are described in U.S. Pat. Nos. 4,994,276, U.S. 5,128,143 and U.S. 5,135,757, hereby incorporated by reference.

The locust bean gum used in the present invention is a galactomannan, i.e., a polysaccharide composed solely of mannose and galactose. Galactomannans which have higher proportions of unsubstituted mannose regions have been found to achieve more interaction with the xanthan gum. Locust bean gum, which has a higher ratio of mannose to the galactose, is especially preferred as compared to other galactomannans such as guar and hydroxypropyl guar.

In certain embodiments, difficulty in obtaining an suitable sustained release rate of moderately and poorly soluble drugs now has been overcome by virtue of the present invention, which is related in part to the surprising discovery that including a pharmaceutically acceptable ionizable gel strength enhancing agent suitable for modifying the release rate from the gel in the sustained release excipient, significantly increases the gel strength of the formulation.

Ionizable gel strength enhancing agents according to the invention may be any pharmaceutically acceptable inorganic or organic ionizable gel strength enhancing agent that is compatible with the gel and that increases the gel strength of the gel matrix formed upon exposure of the solid dosage form to an aqueous environment. This, in turn, prolongs the release of drug from the formulation and prevents a "dose-dumping" effect.

The ionizable gel strength enhancing agent which is optionally used in conjunction with the present invention may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable ionizable gel strength enhancing agent agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride, and hydrates thereof. Multivalent metal cations may also be utilized. Preferred ionizable gel strength enhancing agents are bivalent. In one aspect the ionizable gel strength enhancing agent are calcium sulfate or its dihydrate and sodium chloride. The ionizable gel strength enhancing agents of the present invention are added in an amount effective to obtain a desirable increased gel strength due to the cross-linking of the gelling agent (e.g., the heteropolysaccharide and homopolysaccharide gums).

It is to be understood that the ionizable compound may be a single compound or a mixture of two or more compounds that provide the desired release rates when incorporated in the formulation of the invention.

In certain preferred embodiments of the present invention, the insoluble medicament is rendered more bioavailable, e.g., during manufacture of the dosage form. Preferably, in such embodiments, the insoluble medicament is dispersed into a solid, water soluble carrier to form a solution or dispersion that is thereafter rendered solid to form a "solid solution" or a "solid dispersion" providing improved solubility characteristics for the otherwise insoluble medicament. A solid dispersion is defined as "the dispersion of one or more active ingredients in an inert carrier or matrix at solid-state prepared by the melting (fusion), solvent or melting-solvent method" (W. A. Chiou and R. Riegelman, J. Pharm. Sci., 60, 1281, 1971). Alternatively, Corrigan (O. I. Corrigan, Drug Dev. Inc. Pharm., 11, 697, 1985), has defined the solid dispersion as a "product formed by converting a fluid drug-carrier combination to the solid state." In practice, the term has been synonymous with oral dosage forms, the carrier usually having a higher water solubility than the drug. As used herein, the term "solid dispersion" is considered to be interchangeable with the term "solid solution" since, as a practical matter, it is generally not possible to determine whether the active ingredient is entirely dispersed or partially or fully dissolved in the inert carrier or matrix.

Alternatively, solid solutions or dispersions can be manufactured by (1) a fusion method, which involves heating a physical mixture of the drug and carrier to the fluid state and subsequently cooling to room temperature; (2) a coprecipitation or coevaporation method conducted, e.g., by dissolving the drug and carrier in a volatile organic solvent, followed by evaporation of the solvent, leaving the dispersion as a residue; and (3) a melting-solvent method, e.g., conducted by dissolving the drug within a cosolvent, and mixing the resulting solutions with a molten carrier, followed by cooling of the fluid to room temperature; and any other pharmaceutically acceptable method known to those skilled in the art.

In the present invention, the inert carrier used to prepare the solid solution or dispersion comprises, e.g., a pharmaceutically acceptable solid wetting agent. Mixed surfactant/wetting agent systems are also useful in conjunction with the present invention. Examples of such mixed systems include, for example, sodium lauryl sulfate/solid polyethylene glycol (PEG) 6000 and sodium lauryl sulfate/solid PEG 6000/stearic acid. The artisan will appreciate that any other suitable coating agent may be adjusted to the practice of the inventor. Of course, a solid wetting agent is selected to be pharmaceutically acceptable for oral ingestion.

The solid wetting agent may be dissolved and/or mixed as a slurry in a suitable solvent such as water or ethanol. In certain embodiments, the mixed and/or dissolved wetting agent is thereafter added to the blended mixture of the sustained release excipient (gelling agent and inert diluent) and the medicament. This allows the wetting agent to wet the particles of the excipient such that when the solvent evaporates the particles of the medicament which precipitate are tiny and do not aggregate. Optionally, a hydrophobic material such as ethylcellulose is also added to the slurry. Finally, a sustained release excipient (e.g., a gelling agent and inert diluent) as disclosed herein is added to the slurry. An agglomerated particle or granulate of the medicament and the wetting agent is obtained which is preferably finely and homogeneously dispersed in the sustained release excipient.

In preferred embodiments, the weight to weight ratio of solubilizer to active agent is 1:1 or greater, so that the weight of solubilizer is equal or greater than the weight of drug.

Alternatively, the medicament, e.g. nifedipine, is added to the resultant solution or slurry of wetting agent. While mixing, the medicament-containing solution or slurry is then added to a high shear mixer or granulator containing the sustained release excipient. Ultimately, agglomerated particles containing the medicament are produced by these methods. In one aspect of the process according to the invention, a low solubility medicament is blended, e.g., dry blended, with a sustained release excipient as disclosed herein and then a wetting agent is added to the mixture to form a wetting agent-based slurry which is then dried and milled.

In a further aspect of the process, a wetting agent and then a low solubility medicament, e.g., nifedipine, are added to heated water. A sustained release excipient as disclosed herein is added to the resulting water slurry followed by the optional addition of ethylcellulose.

In certain preferred embodiments of the present invention, the sustained release excipient is prepared by mixing a gelling agent, ionizable gel strength enhancing agent, and an inert diluent. Thereafter, the mixture is granulated with a solution or dispersion of a hydrophobic polymer in an amount effective to slow the hydration of the gelling agent without disrupting the hydrophilic matrix. Next, the insoluble medicament is added, and the resultant mixture is tableted.

The wetting agent is preferably included in an amount effective to provide a final sustained release product having acceptable bioavailability. For example, in certain embodiments of the present invention wherein the medicament is nifedipine, the wetting agent is included in an amount from about 2% to about 20% by weight of the final product. In another aspect, the wetting agent is included in an amount from about 5% to about 10% of the final product, by weight. In a preferred embodiment, the wetting agent as described herein is preferrably a solid polyethylene glycol (PEG) material.

The formulations according to the invention may be prepared by one or more of the following processes, although other, analogous methods may also be used. In one aspect, an oral solid dosage form is prepared according to any method known to the art wherein the therapeutically active medicament is suspended or dissolved in a solid composition comprising, e.g., a wetting agent such as a solid PEG material to produce a solid PEG-water slurry. The solid PEG -water slurry can be prepared as described and granulated with an effective amount of an excipient according to the invention, as previously described, to form a solid dispersion of the therapeutically active medicament, by, e.g., adding an effective amount of low solubility pharmaceutically active medicament to the solid PEG-water slurry. Simply by way of example, this can be accomplished by placing an excipient according to the invention in a high shear mixer/granulator and mixing as necessary for complete mixing, e.g., about two minutes, during which mixing a hydrophobic polymer, e.g., Surelease® (ethylcellulose suspension) may be added. A suitable amount of additional purified water is then added with additional mixing of; e.g., about 1 minute. The mixture is then dry granulated in a fluid bed dryer to a loss on drying ("LOD") of, e.g., less than 7%. The granulation is then optionally milled through 20 mesh screen followed by blending in a V-blender for period of time sufficient to provide a smooth mixture, e.g., about 5 minutes, with sodium stearyl fumarate and then, if desired, compressed into tablets.

In other preferred embodiments of the present invention, the tablets prepared as set forth above are then coated with a hydrophobic polymer to a weight gain from about 1 to about 20 percent by weight.

The inert filler of the sustained release excipient preferably comprises a pharmaceutically acceptable saccharide, including a monosaccharide, a disaccharide, or a polyhydric alcohol, and/or mixtures of any of the foregoing. Examples of suitable inert pharmaceutical fillers include sucrose, dextrose, lactose, microcrystalline cellulose, fructose, xylitol, sorbitol, starches, mixtures thereof and the like. However, it is preferred that a soluble pharmaceutical filler such as lactose, dextrose, sucrose, or mixtures thereof be used. In one aspect the inert diluent or filler is a pre-manufactured direct compression diluent.

For example, it is possible to dry mix the ingredients of the sustained release excipient without utilizing a wet granulation step. This procedure may be utilized, for example, where a wet granulation is to be accomplished when the active ingredient is directed added to the ingredients of the sustained release excipient. On the other hand, this procedure may also be used where no wet granulation step whatsoever is contemplated. If the mixture is to be manufactured without a wet granulation step, and the final mixture is to be tableted, it is preferred that all or part of the inert diluent comprise a pre-manufactured direct compression diluent. Such direct compression diluents are widely used in the pharmaceutical arts, and may be obtained from a wide variety of commercial sources. Examples of such pre-manufactured direct compression excipients include Emcocel® (microcrystalline cellulose, N.F.), Emdex® (dextrates, N.F.), and Tab-Fine® (a number of direct-compression sugars including sucrose, fuctose and dextrose), all of which are commercially available from Edward Mendell Co., Inc., Patterson, N.Y.). Other direct compression diluents include Anhydrous lactose (Lactose N.F., anhydrous direct tableting) from Sheffield Chemical, Union, N.J. 07083; Elcems® G-250 (powdered cellulose), N.F.) from Degussa, D-600 Frankfurt (Main) Germany; Fast-Flo Lactose® (Lactose, N.F., spray dried) from Foremost Whey Products, Banaboo, Wis. 53913; Maltrin® (Agglomerated maltodextrin) from Grain Processing Corp., Muscatine, Iowa 52761; Neosorb 60® (Sorbitol, N.F., direct-compression from Roquet Corp., 645 5th Ave., New York, N.Y. 10022; Nu-Tab® (Compressible sugar, N.F.) from Ingredient Technology, Inc., Pennsauken, N.J. 08110; Polyplasdone XL® (Crospovidone, N.F., cross-linked polyvinylpyrrolidone) from GAF Corp., New York, N.Y. 10020; Primojel® (Sodium starch glycolate, N.F., carboxymethyl starch) from Generichem Corp., Little Falls, N.J. 07424; Solka Floc® (Cellulose floc) from Edward Mendell Co., Carmel , N.Y. 10512; Spray-dried lactose® (Lactose N.F., spray dried) from Foremost Whey Products, Baraboo, Wis. 53913 and DMV Corp., Vehgel, Holland; and Sta-Rx 1500® (Starch 1500) (Pregelatinized starch, N.F., compressible) from Colorcon, Inc., West Point, Pa 19486.

In general, the formulation may be prepared as a directly compressible diluent, for example, by wet granulating, spray drying lactose or as a premixed direct compression diluent by art known methods. For purposes of the present invention, these specially treated inert diluents will be referred to as "directly compressible" inert diluents.

In certain embodiments, the ingredients of the sustained release excipient can be pre-manufactured. However, in other embodiments the active drug can be added to the excipient ingredients and that mixture melt granulated to form a granulation. Finally, where wetting agent is used, the wetting agent comprising the solubilized or dispersed nifedipine can be added directly to the mixture of ingredients.

In further embodiments of the present invention, the directly compressible inert diluent which is used in conjunction with the sustained release pharmaceutical excipient of the present invention is an augmented microcrystalline cellulose as disclosed in U.S. patent application Ser. No. 08/370,576, filed Jan. 9, 1995, and entitled "PHARMACEUTICAL EXCIPIENT HAVING IMPROVED COMPRESSIBILITY", by J. Staniforth, B. Sherwood and E. Hunter, hereby incorporated by reference in its entirety.

In certain embodiments of the present invention, the sustained release excipient comprises from about 10 to about 99 percent by weight of a gelling agent comprising a heteropolysaccharide gum and a homopolysaccharide gum, from about 1 to about 20 percent by weight of an ionizable gel strength enhancing agent, and from about 0 to about 89 percent by weight of an inert pharmaceutical diluent. In other embodiments, the sustained release excipient comprises from about 10 to about 75 percent gelling agent, from about 2 to about 15 percent ionizable gel strength enhancing agent, and from about 30 to about 75 percent inert diluent. In yet other embodiments, the sustained release excipient comprises from about 30 to about 75 percent gelling agent, from about 5 to about 10 percent ionizable gel strength enhancing agent, and from about 15 to about 65 percent inert diluent.

The sustained release excipient of the present invention (with or without the optional ionizable gel strength enhancing agent) may be further modified by incorporation of a pharmaceutically acceptable hydrophobic material which slows the hydration of the gums without disrupting the hydrophilic matrix. This is accomplished in preferred embodiments of the present invention by granulating the sustained release excipient with the solution or dispersion of a pharmaceutically acceptable hydrophobic material prior to the incorporation of the medicament. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The amount of hydrophobic material incorporated into the sustained release excipient is that which is effective to slow the hydration of the gums without disrupting the hydrophilic matrix formed upon exposure to an environmental fluid. In certain preferred embodiments of the present invention, the pharmaceutically acceptable hydrophobic material is included in the sustained release excipient in an amount from about 1 to about 20 percent by weight. The carrier for the hydrophobic material may be an aqueous suspension or an organic solvent, or mixtures thereof. In one aspect, a preferred solvent for the hydrophobic material is ethanol.

Examples of commercially available alkylcelluloses are Aquacoat® (aqueous dispersion of ethylcellulose available from FMC) and Surelease® (aqueous dispersion of ethylcellulose available from Colorcon). Examples of commercially available acrylic polymers suitable for use as the hydrophobic material include Eudragit® RS and RL (copolymers of acrylic and methacrylic acid esters having a low content (e.g, 1:20 or 1:40) of quaternary ammonium compounds).

Agglomeration may be conducted by any art-known technique to yield an acceptable excipient product. In wet granulation techniques, the desired amounts of the xanthan gum, the locust bean gum, and the inert diluent are mixed together and thereafter a moistening agent such as water, polyethylene glycol, glycerol, alcohol or the like is added to prepare a moistened mass. Next, the moistened mass is dried. The dried mass is then milled with conventional equipment into granules. Therefore, the excipient product is ready to use.

The sustained release excipient is preferably free-flowing and directly compressible. Accordingly, the excipient may be mixed in the desired proportion with a therapeutically active medicament and optional lubricant (dry granulation). Alternatively, all or part of the excipient may be subjected to a wet granulation with the active ingredient and thereafter tableted. The medicament may be blended with the excipient, e.g., in a high shear mixer.

In certain especially preferred embodiments, the medicament is a therapeutically effective dihydropyridine. Dihydropyridines are useful for the treatment of circulatory disorders and high blood pressure. Useful formulations of dihydropyridines generally contain doses from about 10 mg to about 240 mg. The production of dihydropyridines is well known in the art, and is described, for example, in British Patent 1,173,862. Other suitable dihydropyridines include, for example, nimodipine, nivaldipine, nitrendipine, nisolidipine, niludipine, nicardipine and felodipine. This list is not meant to be exclusive, and many other dihydropyridines and indeed other medicaments having similar solubility and/or bioavailability problems may also be used successfully in conjunction with the present invention. An especially preferred dihydropyridine is nifedipine. Dihydropyridines such as nifedipine have an aqueous solubility of less than about 1,000 mg/l. Accordingly, in certain preferred embodiments of the present invention, the dosage form includes a dosage of nifedipine in an amount of 20 mg, 30 mg, 60 mg, or 90 mg. Nifedipine (3,5-pyridinedicarboxylic acid, 1,4-dihydro-2,6-dimethyl4-(2-nitrophenyl)-, dimethyl ester, $C_{17}H_{18}N2O_6$; mol. wt 346.3) is a selective inhibitor of calcium influx across cell membranes (e.g., cardiac or arterial wall muscle). Nifedipine is commercially available in a crystalline form (practically insoluble in water but soluble in ethanol) and is typically prescribed as an antianginal agent, although other indications, e.g., migraine headaches, have been tested with some success. Nifedipine is presently commercially available in both immediate release (10 or 20 mg capsules by, e.g., Pfizer) and extended release –24 hour tablets (e.g., 30, 60 and 90 mg tablets by e.g., Pfizer).

During preparation of the formulations of this invention, crystalline nifedipine is preferably rendered into amorphous particles prior to the mixture of the same with any excipients. This is particularly true when the nifedipine is incorporated with a surfactant and then wet granulated with the sustained release excipient of the present invention to produce an agglomerated particle. The nifedipine which is to be incorporated into the formulations of the invention is particulate in nature, and may be in either micronized or unmicronized condition. Generally, those skilled ill the art will appreciate that unmicronized nifedipine tends to have a lower bioavailability than micronized nifedipine. Nifedipine is highly insoluble and, therefore, micronization is deemed to provide more surface area, better absorption, and therefore better bioavailability. Nifedipine is commercially available in micronized form and the average particle size of such nifedipine particles is approximately 10 microns. In certain embodiments of the invention, however, the nifedipine may be subjected to a supermicronization process whereby the average particle size is reduced and the specific surface area is increased.

The hydrophobic material discussed above may be dissolved in an organic solvent or dispersed in an aqueous solution or suspension. Thereafter, the hydrophobic material may be used to coat the granulate of medicament/wetting agent/sustained release excipient. The granulate may be coated with the hydrophobic coating to a weight gain of, e.g., from about 1 to about 20 percent, and preferably from about 5 to about 10 percent. The granulation is then preferably dried. Thereafter, the granulate may be further formulated into an appropriate oral dosage form, for example, by compression of the resulting granulate into appropriately sized tablets, by filling gelatin capsules with an appropriate amount of the granulate (with or without compression of the granulate), as well as use in the manufacture of other oral dosage forms known to those skilled in the art. This embodiment may be particularly beneficial to reduce the amount of drug released during the initial phases of dissolution when the formulation is exposed to fluid in an environment of use, e.g., in-vitro dissolution or in the gastrointestinal tract.

An effective amount of any generally accepted pharmaceutical lubricant, including the calcium or magnesium soaps may be added to the above-mentioned ingredients of the excipient be added at the time the medicament is added, or in any event prior to compression into a said dosage form. An example of a suitable lubricant is magnesium stearate in an amount of about 0.5 to about 3% by weight of the solid dosage form. An especially preferred lubricant is sodium stearyl fumarate, NF, commercially available under the trade name Pruv® from the Edward Mendell Co., Inc.

The sustained release excipients of the present invention have uniform packing characteristics over a range of different particle size distributions and are capable of processing into the final dosage form (e.g., tablets) using either direct compression, following addition of drug and lubricant powder, or conventional wet granulation.

The properties and characteristics of a specific excipient system prepared according to the present invention is dependent in part on the individual characteristics of the homo- and hetero-polysaccharide constituents, in terms of polymer solubility, glass transition temperatures etc., as well as on the synergism both between different homo- and heteropolysaccharides and between the homo and heteropolysaccharides and the inert saccharide constituent(s) in modifying dissolution fluid-excipient interactions.

The combination of the gelling agent with the inert diluent, with or without the ionizable compound and hydrophobic polymer, provides a ready-to-use product in which a formulator need only blend the desired active medicament and an optional lubricant with the excipient and then compress the mixture to form slow release tablets. The excipient may comprise a physical admix of the gums along with a soluble excipient such as compressible sucrose, lactose or dextrose, although it is preferred to granulate or agglomerate the gums with plain (i.e., crystalline) sucrose, lactose, dextrose, etc., to form an excipient. The granulate form has certain advantages including the fact that it can be optimized for flow and compressibility; it can be tableted, formulated in a capsule, extruded and spheronized with an active medicament to form pellets, etc.

When the final product to be manufactured is tablets, the complete mixture, in an amount sufficient to make a uniform batch of tablets, is then subjected to tableting in a conventional production scale tableting machine at normal compression pressure, i.e. about 2000–1600 lbs/sq in. However, the mixture should not be compressed to such a degree that there is subsequent difficulty in its hydration when exposed to gastric fluid.

One of the limitations of direct compression as a method of tablet manufacture is the size of the tablet. If the amount of active agent is high a pharmaceutical formulator may choose to wet granulate the active agent with other excipients to attain a decent size tablet with the optimal compact strength. Usually the amount of filler/binder or excipients needed in wet granulation is less than that in direct compression since the process of wet granulation contributes to some extent toward the desired physical properties of a tablet.

The average tablet size for round tablets is preferably about 300 mg to 750 mg and for capsule-shaped tablets about 750 mg to 1000 mg.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec. Tablets compacted using an instrumented rotary tablet machine have been found to possess strength profiles which are largely independent of the inert saccharide component. Scanning electron photomicrographs of largely tablet surfaces have provided qualitative evidence of extensive plastic deformation on compaction, both at the tablet surface and across the fracture surface, and also show evidence of surface pores through which initial solvent ingress and solution egress may occur.

In certain embodiments of the invention, the tablet is coated with a sufficient amount of a hydrophobic polymer to render the formulation capable of providing a release of the medicament such that a 12 or 24 hour formulation is obtained (or any duration therebetween). The hydrophobic polymer which included in the tablet coating may be the same or different material as compared to the hydrophobic polymeric material which is optionally granulated with the sustained release excipient.

In other embodiments of the present invention, the tablet coating may comprise an enteric coating material in addition to or instead or the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit™ L 100-SSS.

In further embodiments, the dosage form may be coating with a hydrophilic coating in addition to or instead of the above-mentioned coatings. An example of a suitable material which may be used for such a hydrophilic coating is hydroxypropylmethyl-cellulose (e.g., Opadry®, commercially available from Colorcon, West Point, Pa.).

The coatings may be applied in any pharmaceutically acceptable manner known to those skilled in the art. In a preferred embodiment, the coating is applied via a fluidized bed or in a coating pan. The coated tablets may then be dried or cured, e.g., at about 60–70° C. for about 3–4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about $10\mu$ if applied via spray-coating or immersion-coating. Generally, in embodiments of the invention wherein a hydrophobic polymer or enteric coating is applied to the tablets, the tablets are coated to a weight gain from about 1 to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In certain embodiments of the present invention, the tablet core includes an additional dose of the medicament included in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of a therapeutically active agent is needed to provide therapeutically effective blood levels of the active agent when the formulation is first exposed to gastric fluid. The loading dose of medicament included in the coating layer may be, e.g., from about 10% to about 40% of the total amount of medicament included in the formulation.

In a particular embodiment, polyethylene glycol 3350, a solid PEG at room temperature, is mixed with water to form a PEG/water slurry. PEG 3350 is solid before mixing with water. Pre-micronized nifedipine is added to the PEG/water slurry to make a PEG/water/nifedipine mixture. The resulting mixture is mixed with xanthan gum, locust bean gum and diluent and granulated and agglomerated or, alternatively, is added to a pre-prepared granulated and agglomerated excipient formed of xanthan gum, locust bean gum and diluent as described above. The resulting mixture is dried and sieved and may, therefore, be tableted or otherwise prepared in unit dosage form.

DETAILED DESCRIPTION OF THE PREFERRED EMBODIMENTS

The following examples illustrate various aspects of the present invention. They are not to be construed to limit the claims in any manner whatsoever.

EXAMPLES 1–3

Effect of Calcium Sulfate in Excipient

In Example 1–3, sustained release excipients in accordance with the present invention are first prepared, the medicament (in this case nifedipine) being added subsequently, and the final mixture then being tableted.

The sustained release excipient is prepared by dry blending the requisite amounts of xanthan gum, locust bean gum, calcium sulfate, and dextrose in a high speed mixer/granulator for 3 minutes. While running choppers/impellers, water (125–150 ml) is added to the dry blended mixture, and granulated for another 3 minutes. The granulation is then dried in a fluid bed dryer to a LOD (loss on drying) of less than about 10% by weight (e.g., 4–7% LOD). The granulation is then milled using 20 mesh screens. The ingredients of the granulations of Examples 1–3 are set forth in Table 1 below:

TABLE 1

PREPARATION OF SUSTAINED-RELEASE EXCIPIENT

| Component | | % - Ex. 1 | % - Ex. 2 | % - Ex. 3 |
|---|---|---|---|---|
| I. | Xanthan Gum | 25 | 25 | 25 |
| II. | Locust Bean Gum | 25 | 25 | 25 |
| III. | Calcium Sulfate | 0 | 5 | 20 |
| IV. | Dextrose | 50 | 45 | 30 |
| V. | Water | 150 ml | 123 ml | 123 ml |

Next, the sustained release excipient prepared as detailed above is dry blended with the desired amount of nifedipine along with a suitable amount of wetting agent (PEG 3350) in a V-blender for 15 minutes. A suitable tableting lubricant (Pruv®, sodium stearyl fumarate, NF, commercially available from the Edward Mendell Co., Inc.) is added, and the mixture is blended for another 5 minutes. This final mixture is tableted to approximately 361 mg. The ingredients of the tablets of Examples 1–3 are set forth in Table 2 below:

TABLE 2

TABLET FORMULATION - EXAMPLES 1–3

| Component | | % |
|---|---|---|
| A. | Sustained-Release Excipient | 83.1 |
| B. | Nifedipine | 8.31 |
| C. | PEG 3350 | 8.31 |
| D. | Pruv ®* | 0.25 |

*Sodium Stearyl Fumarate

Dissolution tests were then carried out on the tablets of Examples 1–3. The dissolution tests are conducted in 30% polyethyleneglycol (PEG) 400 and distilled water in an automated USP dissolution apparatus (Paddle type 11, 150 rpm), and the amount of drug released was analyzed via UV analysis. The results are set forth in Table 3 below.

TABLE 3

| Time (hr) | Ex. 1 | Ex. 2 | Ex. 3 |
|---|---|---|---|
| 4 | 14.7 | 27.4 | 15.6 |
| 8 | 42.2 | 47.9 | 43.0 |
| 12 | 59.2 | 60.3 | 58.8 |
| 16 | 80.7 | 68.2 | 65.6 |
| 20 | 91.8 | 84.2 | 74.5 |
| 24 | 97.2 | 89.6 | 79.7 |

From the results provided in Table 3, it is evident that the tablets of Examples 1–3 provided suitable 24 hour oral solid dosage forms for nifedipine.

EXAMPLES 4–6

Effect of Compression Force

In Examples 4–6, a sustained release excipient is prepared by dry blending the requisite amounts of xanthan gum, locust bean gum, calcium sulfate, and dextrose in a high speed mixer/granulator for 3 minutes. A slurry of hydrophobic polymer (ethylcellulose) is prepared by dissolving ethyl cellulose in ethyl alcohol. While running choppers/impellers, the slurry is added to the dry blended mixture, and granulated for another 3 minutes. The granulation is then dried in a fluid bed dryer to a LOD (loss on drying) of less than about 10% by weight (e.g., 4–7% LOD). The granulation is then milled using 20 mesh screens. The ingredients of the sustained release excipient of Examples 4–6 ar set forth in Table 4 below:

TABLE 4

| Component | % |
|---|---|
| E. Xanthan Gum | 25 |
| F. Locust Bean Gum | 25 |
| G. Calcium Sulfate | 10 |
| H. Dextrose | 35 |
| I. Ethyl Cellulose | 5 |
| J. Ethyl Alcohol | 10* |

*removed during processing

Thereafter, nifedipine tablets are prepared as follows. A suitable amount of PEG 3350 is mixed with water until dissolved. The desired amount of nifedipine is blended with the sustained release excipient as set forth above in a high shear mixer for 3 minutes, and then the PEG 3350 in water solution is added by spraying while mixing for an additional 2 minutes. Next, a desired amount of Surelease® (aqueous dispersion of ethylcellulose commercially available from Colorcon, Inc., West Point, Pa., USA) is added to the mixture by spraying while mixing for an additional 3 minutes. The granulation is dried in a fluid bed dryer to an LOD of less than 10%. The dried granulation is milled using 20 mesh screens. The dried granulation obtained is tableted to approximately 380 mg using different compression forces. In Example 4, the compression force is 2.5 Kp. In Example 5, the compression force is 12.5 Kp. In Example 6, the compression force is 20.0 Kp. The ingredients (percentage) of the tablets of Examples 4–6 are set forth in Table 5 below:

TABLE 5

| Component | % |
|---|---|
| K. Sustained Release Excipient | 78.9 |
| L. Nifedipine | 7.9 |
| M. PEG 3350 | 7.9 |
| N. Surelease ® | 5.3 |
| O. Water | 16.8* |

*removed during processing

Tablets prepared in accordance with Examples 4–6 are then tested with regard to dissolution (U.S.P. Apparatus III in 30% PEG 400 at 30 cycles/minutes) and the drug released analyzed via a UV analysis procedure as set forth in Examples 1–3. The dissolution results for the tablets of Examples 4–6 are provided in Table 6 below.

TABLE 6

| Time (hr) | Ex. 4 | Ex. 5 | Ex. 6 |
|---|---|---|---|
| 4 | 34.1 | 33.6 | 37.0 |
| 8 | 69.1 | 66.0 | 71.7 |
| 12 | 87.0 | 86.3 | 88.9 |
| 16 | 94.3 | 93.6 | 95.7 |
| 20 | 97.5 | 97.1 | 98.6 |
| 24 | 98.8 | 98.7 | 100.1 |

As is readily apparent from the results provided in Table 6, there was substantially no difference in the release of medicament from the tablets when manufactured using different compression forces.

EXAMPLES 7–9

Effect of Drug:Gum Ratio

In Examples 7–9, a sustained release excipient is prepared in accordance with the procedures set forth for Examples 4–6. The ingredients of the sustained release excipient of Examples 7–9 are set forth in Table 7 below:

TABLE 7

| Component | % |
|---|---|
| P. Xanthan Gum | 25 |
| Q. Locust Bean Gum | 25 |
| R. Calcium Sulfate | 10 |
| S. Dextrose | 35 |
| T. Ethyl Cellulose | 5 |
| U. Ethyl Alcohol | 10* |

*removed during processing

Thereafter, nifedipine tablets are prepared as follows. The sustained release excipient and a suitable amount of nifedipine are blended in a high shear mixer for 3 minutes. PEG 3350 is mixed with Pruv® until dissolved, and the resulting solution is thereafter added to the blend of sustained release excipient and nifedipine by spraying while mixing for an additional minutes. Thereafter, a dispersion of ethylcellulose in ethanol by spraying while mixing for an additional 3 minutes. Then, the granulation is dried in a fluid bed dryer to an LOD of less than 10%. The dried granulation is milled using 20 mesh screens, and tableted to an appropriate weight (about 383 mg, 443 mg and 503 mg for examples 7–9 respectively). The ingredients of the tablets of Examples 7–9 are set forth in Table 8 below:

TABLE 8

| Component | %-Ex. 7 | %-Ex. 8 | %-Ex. 9 |
|---|---|---|---|
| VI. TIMERx ® | 78.4 | 81.3 | 83.5 |
| VII. Nifedipine | 7.8 | 6.8 | 6.0 |
| VIII. PEG 3350 | 7.8 | 6.8 | 6.0 |
| IX. Ethylcellulose | 5.2 | 4.5 | 4.0 |
| X. Pruv ® | 0.8 | 0.7 | 0.6 |

In Example 7, the drug:gum ratio is about 1:5. In Example 8, the drug:gum ratio is about 1:6. In Example 9, the drug:gum ratio is about 1:8. By "gum" it is mea nt the combined weight of xanthan gum and locust bean gum.

Tablets prepared in accordance with Examples 7–9 are then tested with regard to dissolution according to the procedure set forth with respect to Examples 4–6. The dissolution results for the Examples 7–9 are provided in Table 9 below.

TABLE 9

| Time (hr) | Ex. 7 | Ex. 8 | Ex. 9 |
|---|---|---|---|
| 4 | 11.3 | 9.0 | 9.3 |
| 8 | 26.9 | 22.1 | 20.4 |
| 12 | 48.8 | 36.5 | 30.8 |
| 16 | 69.5 | 51.2 | 45.0 |
| 20 | 76.3 | 65.2 | 60.4 |
| 24 | 80.8 | 79.9 | 73.0 |

As can be seen from the results provided in Table 9, the rate of release of nifedipine was slower as the amount of gum relative to the amount of drug increased.

EXAMPLES 10–14

Effect of Gum Content

In Examples 10–14, a sustained release excipient is prepared in accordance with the procedures set forth for Examples 4–6. The ingredients of the sustained release excipient of Examples 10–14 are set forth in Table 10 below:

TABLE 10

| | Percent Included | | | | |
|---|---|---|---|---|---|
| Component | Ex. 10 | Ex. 11 | Ex. 12 | Ex. 13 | Ex. 14 |
| Xanthan Gum | 0 | 5 | 12.5 | 25 | 37.5 |
| Locust Bean Gum | 0 | 5 | 12.5 | 25 | 37.5 |
| Calcium Sulfate | 10 | 10 | 10 | 10 | 10 |
| Dextrose | 85 | 75 | 60 | 35 | 10 |
| Ethyl Cellulose | 5 | 5 | 5 | 5 | 5 |
| Ethyl Alcohol | 10* | 10* | 10* | 10* | 10* |

*removed during processing

Thereafter, nifedipine tablets are prepared in accordance with the procedures set forth with respect to Examples 7–9.

The dried granulation is tableted to an appropriate weight, approximately 383 mg. The final product has the following ingredients set forth in Table 11 below:

TABLE 11

| Component | % |
|---|---|
| A. Sustained-Release Excipient | 78.4 |
| B. Nifedipine | 7.8 |
| C. PEG 3350 | 7.8 |
| D. Ethylcellulose | 5.2 |
| E. Pruv ® | 0.8 |

Tablets prepared in accordance with Examples 10–14 are then tested with regard to dissolution according to the procedure set forth with respect to Examples 4–6. The dissolution results for the Examples 10–14 are provided in Tables 12 and 13 below.

TABLE 12

| Dissolution Time (hr) | Ex. 10 | Ex. 11 | Ex. 12 | Ex. 13 | Ex.14 |
|---|---|---|---|---|---|
| 4 | 91.7 | 49.3 | 34.1 | 21.8 | 24.0 |
| 8 | 91.7 | 85.8 | 69.1 | 59.4 | 49.9 |
| 12 | 91.7 | 91.1 | 87.0 | 84.8 | 83.8 |
| 16 | 91.7 | 93.1 | 94.3 | 101.3 | 91.2 |
| 20 | 91.7 | 93.1 | 97.5 | 105.3 | 92.9 |
| 24 | 91.7 | 93.1 | 98.8 | 106.5 | 92.9 |

TABLE 13

| Dissolution Rate Time (hr) | Ex. 10 | Ex. 11 | Ex. 12 | Ex. 13 | Ex. 14 |
|---|---|---|---|---|---|
| 4 | 91.7 | 49.3 | 34.1 | 21.8 | 24.0 |
| 8 | 0.0 | 36.5 | 35.0 | 37.6 | 25.9 |
| 12 | 0.0 | 5.3 | 17.9 | 25.4 | 33.9 |
| 16 | 0.0 | 2.0 | 7.3 | 16.5 | 7.4 |
| 20 | 0.0 | 0.0 | 3.2 | 4.0 | 1.7 |
| 24 | 0.0 | 0.0 | 1.3 | 1.2 | 0.0 |

As can be seen from the results provided in Tables 12 and 13, substantially all of the nifedipine was released from the tablets of Example 10 (no gum) and Example 11 (10% gum) in about 4 hours and about 12 hours respectively. Therefore, the tablets of Example 11 might represent a suitable 12 hour preparation. The tablets of Examples 12–14, in contrast, provided a dissolution profile which released the nifedipine over a significantly longer period of time compared to the tablets of Example 11. The tablets of Example 14 (75% gum) did not appear to release 100% of the nifedipine at the end of 24 hours.

EXAMPLE 15

Effect of Coating with Hydrophobic Polymer

In Example 15, a sustained release excipient is prepared in accordance with the procedures set forth for Examples 4–6. The ingredients of the sustained release excipient of Example 15 are set forth in Table 14 below:

TABLE 14

| Component | % |
|---|---|
| 1. Xanthan Gum | 25 |
| 2. Locust Bean Gum | 25 |
| 3. Compactrol | 10 |
| 4. Emdex | 35 |
| 5. Ethyl Cellulose | 5 |
| 6. Ethyl Alcohol | 5* |

*removed during processing

Thereafter, nifedipine tablets are prepared in accordance with the procedures set forth with respect to Examples 4–6. The dried granulation is tableted to approximately 380 mg (target weight is 382.5 mg). The ingredients for the tablets of Example 15 are set forth in Table 15 below.

TABLE 15

| Component | % |
|---|---|
| F. Sustained-Release Excipient | 78.44 |
| G. Nifedipine | 7.84 |
| H. PEG 3350 | 7.84 |
| I. Pruv ® | 0.24 |
| J. Surelease ® | 5.64 |
| K. Ethyl Alcohol | (75 ml)* |

*removed during processing

Thereafter, a portion of the tablets are coated with a hydrophobic polymer. To accomplish this, ethyleellulose (Surelease®, 400 g) is mixed with water (100 g) to form an aqueous suspension. Thereafter, the tablets are coated in a Keith Machinery coating pan (diameter 350 mm; pan speed 20 rpm; spray-gun nozzle 0.8 mm; tablets bed temperature 40°–50° C.; charge per batch 1 kg; dry air—Conair Prostyle 1250, 60°–70° C.). The tablets are coated to a weight gain of about 5%.

Tablets prepared in accordance with Example 15 are then tested with regard to dissolution according to the procedure utilizing USP Method 111 (USP XXII) at 15 cpm, in 100 ml of distilled water, and the amount of drug released is assayed using an HPLC procedure as set forth below.

The assay method for the nifedipine tablets is as follows:

Mobile phase—Prepare a suitable mixture of water, acetonitrile, and methanol (40:30:30), and degas. Make adjustments if necessary. (Rf. USP XXII, P. 946).

Standard preparation—Dissolve an accurately weighted quantity of USP Nifedipine RS in the methanol (about 1 mg/ml), and dilute with mobile phase to obtain a solution having a known concentration of about 0.1 mg, per ml.

Assay preparation—Weigh and finely powder not less than 20 tablets. Transfer an accurately weighed portion of the powder, equivalent to about 25 mg of Nifedipine to a 250 ml.-volumetric flask. Add about half volume of mobile phase, shake for 15 minutes and sonicate for 15 minutes. Filter through medium-porosity filter paper, wash the remainder with mobile phase up to the volume mark. Mix the solution before use.

Chromatographic system—The liquid chromatograph is equipped with a 265 nm detector and a 25-cm×4.6-mm column that contains 5 μm packing L1. The flow rate is about 1.0-ml per minute. (Cf. Chromatograph the standard preparation, and record the peak responses as directed under procedure. The column efficiency is not less than 16,000 theoretical plates per meter, the tailing factor is not less than 1.5, and the relative standard deviation of the response of the main peak is not more than 1.0%.

Procedure—Separately inject equal volumes (about 25 μL) of the standard preparation and the assay preparation into the chromatograph, record the chromatograms, and measure the response for the major peak. Calculate the quantity, in mg, of C H N O in the portion of nifedipine taken by the formula:

$$250C(Ru/RS)_2$$

in which C is the concentration, in mg per ml, of USP Nifedipine RS in the standard preparation, and Ru and Rs are the peak response obtained from assay preparation and standard preparation, respectively.

The dissolution results for Example 15A (uncoated tablets) and Example 15 (coated) and are provided in Table 16 below.

TABLE 16

| | Percent Dissolved | |
|---|---|---|
| Time (hr) | Ex. 15A | Ex. 15 |
| 4 | 12.76 | 13.53 |
| 8 | 36.89 | 42.99 |
| 12 | 73.06 | 63.27 |
| 16 | 98.07 | 73.69 |
| 20 | 102.07 | 78.95 |
| 24 | 106.33 | 87.88 |

EXAMPLE 16

Preparation of Once-Daily 30 mg Oral Nifedipine Formulation with Pre-Granulation Dry Blending Step Addition An oral once-daily 30 mg nifedipine formulation was prepared as follows:

Equipment
Granulator: Baker-Perkins 10L high shear mixer/granulator
Dryer: Aeromatic Strea 1 fluid bed dryer
Tablet press: Stokes RB2 16 station rotary press
V Blender: Patterson-Kelley 2 quart blender

TABLE 17

PREPARATION OF SUSTAINED RELEASE EXCIPIENT

| | Component | Amount (%) |
|---|---|---|
| 1. | Xanthan gum | 25 |
| 2. | Locust bean gum | 25 |
| 3. | Dextrose | 35 |
| 4. | Calcium sulfate, dihydrate | 10 |
| 5 | Ethylcellulose | 5 |
| 6. | Ethanol | 15* |

*Removed during processing

Procedure:
1. Dissolve (5) in (6).
2. Dry blend (1), (2), (3), and (4) in high speed mixer/granulator for 2 minutes.
3. While running choppers/impeller, add slurry from Step (1) above.
4. Granulate for another 2 minutes.
5. Dry granulation in fluid bed dryer to LOD between 4 and 7%.
6. Mill through 20 mesh screen.

The sustained release excipient of Table 17 was then used in the formulation as follows:

TABLE 18

| Component | Amount (%) |
|---|---|
| 1. Sustained Release Excipient | 79 |
| 2. Nifedipine | 7 |
| 3. PEG 3350 | 8 |
| 4. Surelease ® | 5 |
| 5. Sodium stearyl fumarate | 1 |
| 6. Purified water | 13* |

*Removed during processing

Procedure:
1. Dissolve (3) in (6).
2. Dry blend (1) and (2) in high shear mixer/granulator for 3 minutes.
3. While mixing, add slurry from Step (1) above. Blend 0.5 minutes.
4. While mixing, add (4). Blend 0.5 minutes.
5. Mix another 2 minutes.
6. Dry granulation in fluid bed dryer to LOD less than 7%.
7. Mill through 20 mesh screen.
8. Place milled material into V-blender.
9. Add (5). Dry blend for 5 minutes.
10. Compress into tablets using ⅜" diameter punches.
Results:
Apparatus: Type III
Media: 30% PEG
Agitation: 15 cpm
Volume: 250 mL

TABLE 19

| DISSOLUTION RESULTS | |
|---|---|
| Time (Hours) | % Dissolved |
| 0 | 0 |
| 4 | 14.2 |
| 8 | 31.5 |
| 12 | 50.4 |
| 16 | 68.9 |
| 20 | 84.7 |
| 24 | 91.7 |
| Tabletweight(mg) | 453.6 |
| Diameter (in) | ⅜" |
| Hardness (Kp) | 7.0 |
| Drug:Gum | 1:6 |

EXAMPLE 17

Preparation of Once-Daily 30 mg Oral Nifedipine Formulation with Pre-And Post-Granulation Dry Blending Step A once-daily 30 mg nifedipine formulation was prepared using the sustained release excipient of Example 16 as follows:

TABLE 20

| Component | Amount % |
|---|---|
| 1. Sustained release excipient | 79 |
| 2. Nifedipine | 7 |
| 3. PEG 3350 | 8 |
| 4. Surelease ® | 5 |
| 5. Sodium stearyl fumarate | 1 |
| 6. Purified water 1 | 8* |
| 7. Purified water 2 | 5* |

*Removed during processing

Procedure:
1. Dissolve (3) in (6).
2. Add (2) to slurry from Step (1) above.
3. Place (1) in high shear mixer/granulator.
4. While mixing, add slurry from Step (2).
5. Add (4).
6. Blend for 2 minutes.
7. Add (7).
8. Mix for additional 1 minute.
9. Dry granulation in fluid bed dryer to LOD less than 7%.
10. Mill through 20 mesh screen.
11. Place milled material into V-blender.
12. Add (5). Dry blend for 5 minutes.
13. Compress into tablets using ⅜" diameter punches.
Results:
Apparatus: Type 111
Media: 30% PEG
Agitation: 15 cpm
Volume: 250 mL

TABLE 21

| DISSOLUTION RESULTS | |
|---|---|
| Time (hours) | % Dissolved |
| 0 | 0 |
| 4 | 12.1 |
| 8 | 25.9 |
| 12 | 43.8 |
| 16 | 69.6 |
| 20 | 82.1 |
| 24 | 88.3 |
| Tabletweight(mg) | 453.6 |
| Diameter (in) | ⅜" |
| Hardness (Kp) | 5.5 |
| Drug:Gum | 1:6 |

EXAMPLE 18

Preparation of Once-Daily 30 mg Oral Nifedipine Formulation with Surelease® Addition After High Shear/Mixer Step A once-daily 30 mg nifedipine formulation was prepared using the sustained release excipient of Example 16 as follows:

TABLE 22

| Component | Amount % |
|---|---|
| 1. Sustained release excipient | 79 |
| 2. Nifedipine | 7 |
| 3. PEG 3350 | 8 |

TABLE 22-continued

| Component | Amount % |
|---|---|
| 4. Surelease ® | 5 |
| 5. Sodium stearyl fumarate | 1 |
| 6. Purified water 1 | 8* |
| 7. Purified water 2 | 5* |

*Removed during processing

Procedure:
1. Dissolve (3) in (6).
2. Add (2) to slurry from Step (1) above. Mix.
3. Add (4) to slurry from Step (2) above. Mix.
4. Place (1) in high shear mixer/granulator.
5. While mixing, add slurry from Step (3).
6. Mix for 2 minutes.
7. Add (7).
8. Mix for additional 1 minute.
9. Dry granulation in fluid bed dryer to LOD less than 7%.
10. Mill through 20 mesh screen.
11. Place milled material into V-blender.
12. Add (5). Dry blend for 5 minutes.
13. Compress into tablets using ⅜" diameter punches.

Results:
Apparatus: Type III
Media: 30% PEG
Agitation: 15 cpm
Volume: 250 mL

TABLE 23

| Time (hours) | % Dissolved |
|---|---|
| 0 | 0 |
| 4 | 11.8 |
| 8 | 30.3 |
| 12 | 51.7 |
| 16 | 77.2 |
| 20 | 86.7 |
| 24 | 91.8 |
| Tabletweight(mg) | 453.6 |
| Diameter (in) | ⅜" |
| Hardness (Kp) | 5.9 |
| Drug:Gum | 1:6 |

EXAMPLE 19

Preparation of Once-Daily 30 mg Oral Nifedipine Formulation with PEG 400

A once-daily 30 mg nifedipine formulation was prepared using the sustained release excipient of Example 16 as follows:

TABLE 24

| Component | Amount % |
|---|---|
| 1. Sustained Release Excipient | 74 |
| 2. Nifedipine | 6 |
| 3. PEG 400 | 14 |
| 4. Surelease ® | 5 |
| 5. Sodium stearyl fumarate | 1 |

Procedure:
1. Dissolve (2) in (3).
2. Place (1) in high shear mixer/granulator.
3. While mixing, add slurry from Step (1).
4. Add (4) and mix for 2 minutes.
5. Dry granulation in fluid bed dryer to LOD less than 7%.
6. Mill through 20 mesh screen.
7. Place milled material into V-blender.
8. Add (5). Dry blend for 5 minutes.
9. Compress into tablets using ⅜" diameter punches.

Results:
Apparatus: Type III
Media: 30% PEG
Agitation: 15 cpm
Volume: 250 mL

TABLE 25

| Time (hours) | % Dissolved |
|---|---|
| 0 | 0 |
| 4 | 15.6 |
| 8 | 46.1 |
| 12 | 66.4 |
| 16 | 83.6 |
| 20 | 92.1 |
| 24 | 94.6 |
| Tabletweight(mg) | 487.8 |
| Diameter (in) | ⅜" |
| Hardness (Kp) | 2.6 |
| Drug:Gum | 1:6 |

EXAMPLE 20

Preparation of Once-Daily 30 mg Oral Nifedipin, Formulation with PEG 3350

Preparation

A once-daily 30 mg nifedipine formulation was prepared using the sustained release excipient of Example 16 as follows:

TABLE 26

| Component | Amount % |
|---|---|
| 1. Sustained Release Excipient | 76 |
| 2. Nifedipine | 6 |
| 3. PEG 3350 | 12 |
| 4. Surelease ® | 5 |
| 5. Sodium stearyl fumarate | 1 |
| 6. Purified water | 12 |

*Remove during processing

Procedure
1. Heat (6) to 60° C.
2. Add (3) to heated (6). Mix well.
3. Add (2) to slurry from Step (2) above. Mix well.
4. Place (1) in high shear mixer/granulator.
5. While mixing, add slurry from Step (3).
6. Add 4 and mix for 2 minutes.
7. Dry granulation in fluid bed dryer to LOD less than 7%.
8. Mill through 20 mesh screen.
9. Place milled material into V-blender.
10. Add (5). Dry blend for 5 minutes.

Results:

Apparatus: Type III
Media: 30% PEG

Agitation: 15 cpm
Volume: 250 mL

TABLE 27

DISSOLUTION RESULTS

| Time (hours) | % Dissolved |
|---|---|
| 0 | 0 |
| 4 | 12.7 |
| 8 | 27.7 |
| 12 | 46.1 |
| 16 | 66.2 |
| 20 | 82.1 |
| 24 | 88.6 |
| Tabletweight(mg) | 476.6 |
| Diameter (in) | ⅜" |
| Hardness (Kp) | 8.7 |
| Drug:Gum | 1:6 |

EXAMPLE 21

Additional Measurements of 30 mg Oral Nifedipine Formulations

The following data were generated during the development of a once-daily 30 mg nifedipine formulation.

TABLE 28

| Component | Amount % |
|---|---|
| 1. TIMERx | 75 |
| 2. Nifedipine | 7 |
| 3. PEG 3350 | 12 |
| 4. Surelease ® | 5 |
| 5. Sodium stearyl fumarate | 1 |
| 6. Purified water | 13* |

Procedure:
1. Heat (6) to 60° C.
2. Add (3) to heated (6). Mix well.
3. Add (2) to slurry from Step 2 above. Mix well.
4. Place (1) in high shear mixer/granulator.
5. While mixing, add slurry from Step (3).
6. Add (4) and mix for 2 minutes.
7. Dry granulation in fluid bed dryer to LOD less than 7%.
8. Mill through 20 mesh screen.
9. Place milled material into V-blender.
10. Add (5). Dry blend for 5 minutes.
11. Compress into tablets using ⅜" diameter punches.

Results:
Apparatus: Type 111
Media: 30% PEG
Agitation: 15 cpm
Volume: 250 mL

TABLE 29

DISSOLUTION RESULTS

| Time (hours) | % Dissolved |
|---|---|
| 0 | 0.0 |
| 4 | 15.5 |
| 8 | 34.1 |
| 12 | 51.2 |
| 16 | 70.4 |
| 20 | 86.1 |
| 24 | 92.6 |
| Tabletweight(mg) | 403.4 |

TABLE 29-continued

DISSOLUTION RESULTS

| Time (hours) | % Dissolved |
|---|---|
| Diameter (in) | ⅜" |
| Hardness(Kp) | 8.6 |
| Drug:Gum | 1:5 |

Preparation of sustained release excipient used in Examples 21 and 22:

Sustained Release Excipient Used in Examples 21 and 22

| Component | Percent in Matrix Lot 152-009 |
|---|---|
| 1. Xanthan Gum | 25 |
| 2. Locust Bean Gum | 25 |
| 3. Dextrose | 35 |
| 4. Calcium Sulfate | 10 |
| 5. Ethyl Cellulose | 5 |
| 6. Ethyl Alcohol | 10* |

*Removed during processing.

Procedure:

1. Disperse (5) in (6).
2. Dry blend (1), (2), (3) and (4) in high shear mixer/granulator for 3 minutes.
3. White running choppers/impellers, add slurry from Step 1 above.
4. Granulate for 3 minutes.
5. Dry the granulation in fluid bed dryer to LOD of 4–7%.
6. Mill through 20 mesh screen.
  a. Preparation of TIMERx Nifedipine Tablets

| Component | Percent in Tablet Lot 152-009 |
|---|---|
| 1. Sustained Release Excipient | 78.2 |
| 2. Nifedipine | 7.8 |
| 3. PEG | 7.8 |
| 4. Surelease ® | 5.2** |
| 5. Sodium stearyl fumarate | 1.0 |
| 6. Purified water | 13.3* |

*Removed during processing.
**Amount (%) of solids in ethanolic suspension.

Procedure:

1. Disperse (3) in (6).
2. Dry blend (1) and (2) in high shear mixer/granulator for 3 minutes.
3. While mixing, add solution from Step 1 above to blend, and mix for 30 seconds.
4. While mixing, add (4), and mix for 30 seconds.
5. Dry granulation in fluid bed dryer to LOD of <7%.
6. Mill through 20 mesh screen.
7. Add (5) to blend, and mix for 5 minutes in V-blender.
8. Compress into tablets.

EXAMPLE 22

Preparation of A 30 mg Oral Tablet By Dry Granulation Of Xanthan Bean Gum, Locust Bean Gum, Dextrose and Calcium Salt A once-daily 30 mg nifedipine formulation was prepared using the sustained release excipient of Example 21 as follows:

| Component | Percent in Tablet |
|---|---|
| 1. Xanthan Gum | 25 |
| 2. Locust Bean Gum | 25 |
| 3. Dextrose | 35 |
| 4. Calcium Sulfate | 10 |
| 5. Ethyl Cellulose | 5 |
| 6. Ethyl Alcohol | 10* |

*Removed during processing.

Procedure:
1. Disperse (5) in (6).
2. Dry blend (1), (2), (3) and (4) in high shear mixer/granulator for 3 minutes.
3. While running choppers/impellers, add slurry from Step 1 above.
4. Granulate for 3 minutes.
5. Dry the granulation in fluid bed dryer to LOD of 4–7%.
6. Mill through 20 mesh screen.

| Component | Percent in Tablet |
|---|---|
| 1. Sustained Release Excipient | 79.4 |
| 2. Nifedipine | 6.6 |
| 3. wax | 7.8 |
| 4. Surelease ® | 5.2** |
| 5. Sodium stearyl fumarate | 1.0 |
| 6. Purified water | 13.3* |

*Removed during processing.
**Amount (%) of solids in ethanolic suspension.

Procedure:
1. Disperse (3) in (6).
2. Dry blend (I) and (2) in high shear mixer/granulator for 3 minutes.
3. While mixing, add solution from Step 1 above to blend, and mix for 30 seconds.
4. While mixing, add (4), and mix for 30 seconds.
5. Dry granulation in fluid bed dryer to LOD of <7%.
6. Mill through 20 mesh screen.
7. Add (5) to blend, and mix for 5 minutes in V-blender.
8. Compress into tablets.

EXAMPLE 23

Tablets Coated with Hydrophobic Polymer

The tablets prepared in accordance with each of Examples 16–22 are coated with a hydrophobic polymer (ethylcellulose) according to the procedures set forth in Example 15. The tablets are coated to a weight gain of about 5%. Dissolution testing reveals that each of the ethylcellulose coated tablets of examples 16–22 provide suitable 24 hour formulations of nifedipine.

EXAMPLE 24

Tablets Coated with Enteric Polymer

The tablets prepared in accordance with each of Examples 16–22 are coated with an enteric polymer (cellulose acetate phthalate) in accordance with procedures well-known to those of ordinary skill in the art. The tablets are coated to a weight gain of about 5%. Dissolution testing reveals that each of the cellulose acetate phthalate-coated tablets of Examples 16–22 provide suitable 24 hour enteric formulations of nifedipine.

Conclusion

The examples provided above are not meant to be exclusive. Many other variations of the present invention would be obvious to those skilled in the art, and are contemplated to be within the scope of the appended claims. Various publications are cited herein, the disclosures of which are incorporated by reference in their entireties.

What is claimed is:

1. A method of preparing a bioavailable sustained release oral dosage form comprising
   combining (i) a medicament in amorphous form, (ii) a wetting agent and (iii) a sustained release excipient to obtain a mixture; said sustained release excipient comprising a gelling agent, an ionizable gel enhancing agent, and an inert diluent, the ratio of inert diluent to gelling agent being from about 1:8 to about 8:1; said ionizable gel strength enhancing agent increasing the gel strength of a gel formed when said solid dosage form is exposed to an aqueous solution, said gelling agent comprising xanthan gum and locust bean gum in a ratio of said xanthan gum to said locust bean gum of from about 1:3 to about 3:1 and the ratio of said medicament to said gelling agent being from about 1:3 to about 1:8;
   thereafter drying and milling said mixture to obtain a sustained release product; and
   then forming said sustained release product into orally administrable unit doses.

2. The method of claim 1, wherein the medicament has an aqueous solubility of less than 10 g/liter.

3. The method of claim 1, wherein the wetting agent is polyethylene glycol.

4. The method of claim 1, wherein said medicament is selected from the group consisting of nifedipine, nimodipine, nivadipine, nitrendipine, nisolidipine, niludipine, nicardipine and felodipine.

5. The method of claim 4 wherein said medicament is nifedipine.

6. The method of claim 3 wherein the polyethylene glycol is mixed with water to form a polyethylene glycol-water slurry prior to its being combined with the medicament and the sustained release excipient.

7. The method of claim 1, wherein said mixture of medicament, gelling agent, ionizable gel enhancing agent and inert diluent are premanufactured as a sustained release excipient.

8. The method of claim 1, further comprising dissolving the medicament in the wetting agent and then adding the gelling agent, ionizable gel enhancing agent, inert diluent and a hydrophobic material to the resulting combination.

9. The method of claim 1 wherein said gelling agent further comprises an agent selected from the group consisting of alginates, carrageenan, pectin, guar gum, xanthan gum, locust bean gum, modified starch, a cellulosic material and mixtures of any of the foregoing.

10. The method of claim 9, wherein said cellulosic material is selected from the group consisting of hydroxypropylmethylcellulose, methylcellulose, sodium carboxymethylcellulose and hydroxypropyl cellulose and mixtures of any of the foregoing.

11. The method of claim 1, wherein said ionizable gel strength enhancing agent is selected from the group consisting of monovalent, divalent and multivalent organic or inorganic salts and mixture thereof.

12. The method of claim 1, wherein said ionizable gel strength enhancing agent is selected from the group consisting of an alkali metal sulfate, alkali metal chloride, alkali metal borate, alkali metal bromide, alkali metal citrate, alkali metal acetate, alkali metal lactate, alkaline earth metal sulfate, alkaline earth metal chloride, alkaline earth metal borate, alkaline earth metal bromide, alkaline earth metal citrate, alkaline earth metal acetate, alkaline earth metal lactate and mixtures thereof.

13. The method of claim 1, wherein said composition further comprises an amount of a pharmaceutically acceptable hydrophobic material effective to slow the hydration of the gelling agent when said solid dosage form is exposed to gastrointestinal fluid.

14. A method of treating a patient comprising administering a dosage form prepared according to claim 1 to a patient in need of antihypertensive treatment.

15. A method of preparing a bioavailable sustained release oral dosage form comprising:
combining a hydrophobic material and a sustained release excipient comprising a gelling agent, an ionizable gel enhancing agent and an inert diluent, the ratio of inert diluent to gelling agent being from about 1:8 to about 8:1, said ionizable gel strength enhancing agent increasing the gel strength of a gel formed when said solid dosage form is exposed to an aqueous solution, said gelling agent comprising xanthan gum and locust bean gum in a ratio of said xanthan gum to said locust bean gum of from about 1:3 to about 3:1 and the ratio of said medicament to said gelling agent being from about 1:3 to about 1:8;
combining said hydrophobic material and sustained release excipient with (i) a medicament in amorphous form and (ii) a wetting agent to obtain a mixture;
drying and milling said mixture to obtain a sustained release product; and
dividing said sustained release product into orally administrable unit doses.

16. A method of preparing a bioavailable sustained release oral dosage form comprising:
dry blending a medicament in amorphous form and a sustained release excipient to obtain a sustained release product; said sustained release excipient comprising a gelling agent comprising xanthan gum and locust bean gum in a ratio of said xanthan gum to said locust bean gum of from about 1:3 to about 3:1, an ionizable gel enhancing agent which increases the gel strength of a gel formed when said solid dosage form is exposed to an aqueous solution, and an inert diluent, the ratio of inert diluent to gelling agent being from about 1:8 to about 8:1; the ratio of said medicament to said gelling agent being from about 1:3 to about 1:8; and
dividing said sustained release product into orally administrable unit doses.

17. The method of claim 16, further comprising admixing a wetting agent with the dry blended mixture of medicament, gelling agent, ionizable gel enhancing agent and inert diluent to form a wetting agent-based slurry, and then drying and milling the resultant mixture.

18. The method of claim 17, wherein said gelling agent, ionizable gel enhancing agent and inert diluent are precombined as a sustained release excipient.—

19. The method of claim 1, wherein the wetting agent is a mixed surfactant/wetting agent system.

20. The method of claim 1, wherein the medicament is nifedipine and the wetting agent is included in an amount from about 2% to about 20%, by weight, of said sustained release product.

21. The method of claim 13, wherein the unit doses of a sustained release oral solid dosage form are coated with a hydrophobic polymer to a weight gain from about 1% to about 20%, by weight.

22. The method of claim 13, wherein the hydrophobic material is selected from the group consisting of an alkylcellulose, hydrophobic cellulosic materials, polymers or copolymers derived from acrylic or methacrylic acid esters, copolymers of acrylic and methacrylic acid esters, zein, waxes, shellac, and hydrogenated vegetable oils.

23. The method of claim 13, wherein the pharmaceutically acceptable hydrophobic material is included in the sustained release excipient in an amount from about 1 to about 20 percent by weight.

24. The method of claim 13, wherein the hydrophobic material is ethyl cellulose.

25. The method of claim 1, further comprising the step of coating the orally administrable unit doses with a hydrophobic coating.

26. The method of claim 1, wherein the oral solid dosage form is coated with an enteric coating material.

27. The method of claim 1, wherein the oral solid dosage form is coated with a hydrophilic coating.

28. The method of claim 27 wherein the hydrophilic coating is hydroxypropylmethylcellulose.

29. The method of claim 15, wherein the hydrophobic material is ethyl cellulose.

30. The method of claim 1, wherein the sustained release oral dosage form provides a therapeutic effect of medicament for about 12 to about 24 hours.

* * * * *